Figure 1:
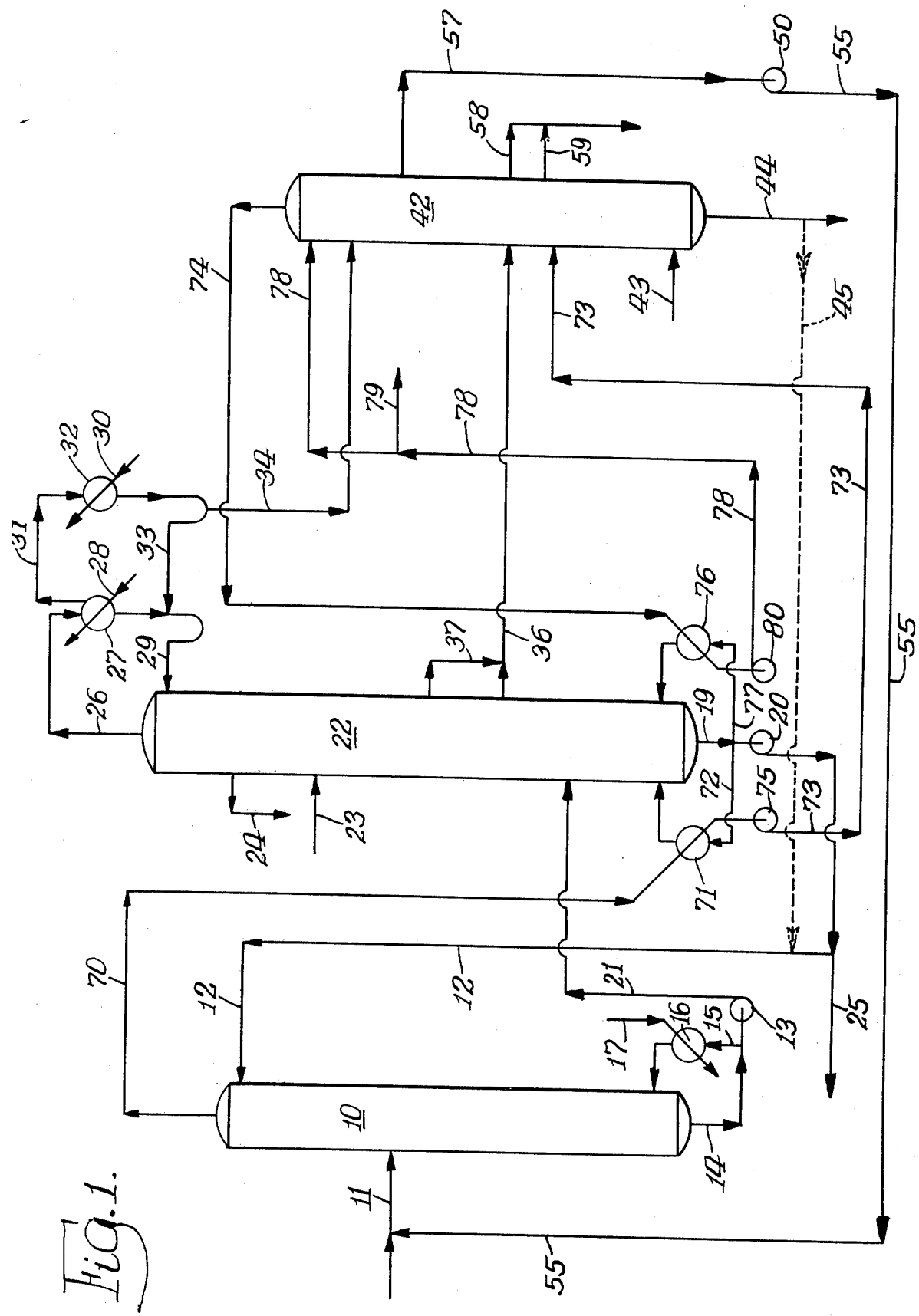

United States Patent [19]
Katzen et al.

[11] 3,990,952
[45] Nov. 9, 1976

[54] ALCOHOL DISTILLATION PROCESS

[75] Inventors: Raphael Katzen; Vincent B. Diebold, both of Cincinnati, Ohio

[73] Assignee: Raphael Katzen Associates International, Inc., Cincinnati, Ohio

[22] Filed: Oct. 10, 1974

[21] Appl. No.: 513,763

[52] U.S. Cl. .................................. 203/33; 203/36; 203/37; 203/84; 203/85; 203/97; 260/643 R
[51] Int. Cl.² .................... C07C 29/24; B01D 3/34
[58] Field of Search .................. 203/36, 37, 85, 33, 203/53, 84, 96, 97; 260/643 E, 643 R

[56] References Cited
UNITED STATES PATENTS

| 1,831,425 | 11/1931 | Ricard .................... 203/37 |
| 2,207,111 | 7/1940 | Rodenberg ............... 203/37 |
| 2,666,735 | 1/1954 | Morrell et al. ........... 203/37 |
| 2,696,463 | 12/1954 | Baevsky .................. 203/37 |
| 3,230,156 | 1/1966 | Katzen .................... 203/37 |
| 3,265,594 | 8/1966 | De Jean et al. ......... 203/85 |
| 3,445,345 | 5/1969 | Katzen et al. .......... 203/85 |

FOREIGN PATENTS OR APPLICATIONS 2,106,073  8/1972  Germany .................... 203/37

*Primary Examiner*—Hiram H. Bernstein
*Attorney, Agent, or Firm*—Hibben, Noyes & Bicknell

[57] ABSTRACT

A crude alcohol-containing mixture comprising a saturated aliphatic alcohol of not more than three carbon atoms and associated impurities is processed in a three-tower distillation system to permit recovery of the desired alcohol product in highly concentrated and purified form. In the first tower the crude feed is subjected to extractive distillation with water to remove substantially all the impurities overhead. An aqueous bottoms stream from the first tower containing 5 to 10 wt.% alcohol and only minor amount of impurities is fed to the second tower where the alcohol product is concentrated and recovered. Overhead and intermediate purge streams containing low boiling and high boiling impurities are removed from the second tower and are fed to the third tower along with the overhead from the first tower. Stripped aqueous effluent is withdrawn from the bottom of the second tower and is recycled in part to the first tower. An aqueous alkali solution is introduced into the second tower and regulated so that the concentration of alkali in the stripped aqueous effluent from the bottom of the tower is from about 0.10 to about 0.24 gram per liter. The impurities are recovered as by-products from the third tower, and an alcohol stream is recycled from the third tower to the first tower.

16 Claims, 2 Drawing Figures

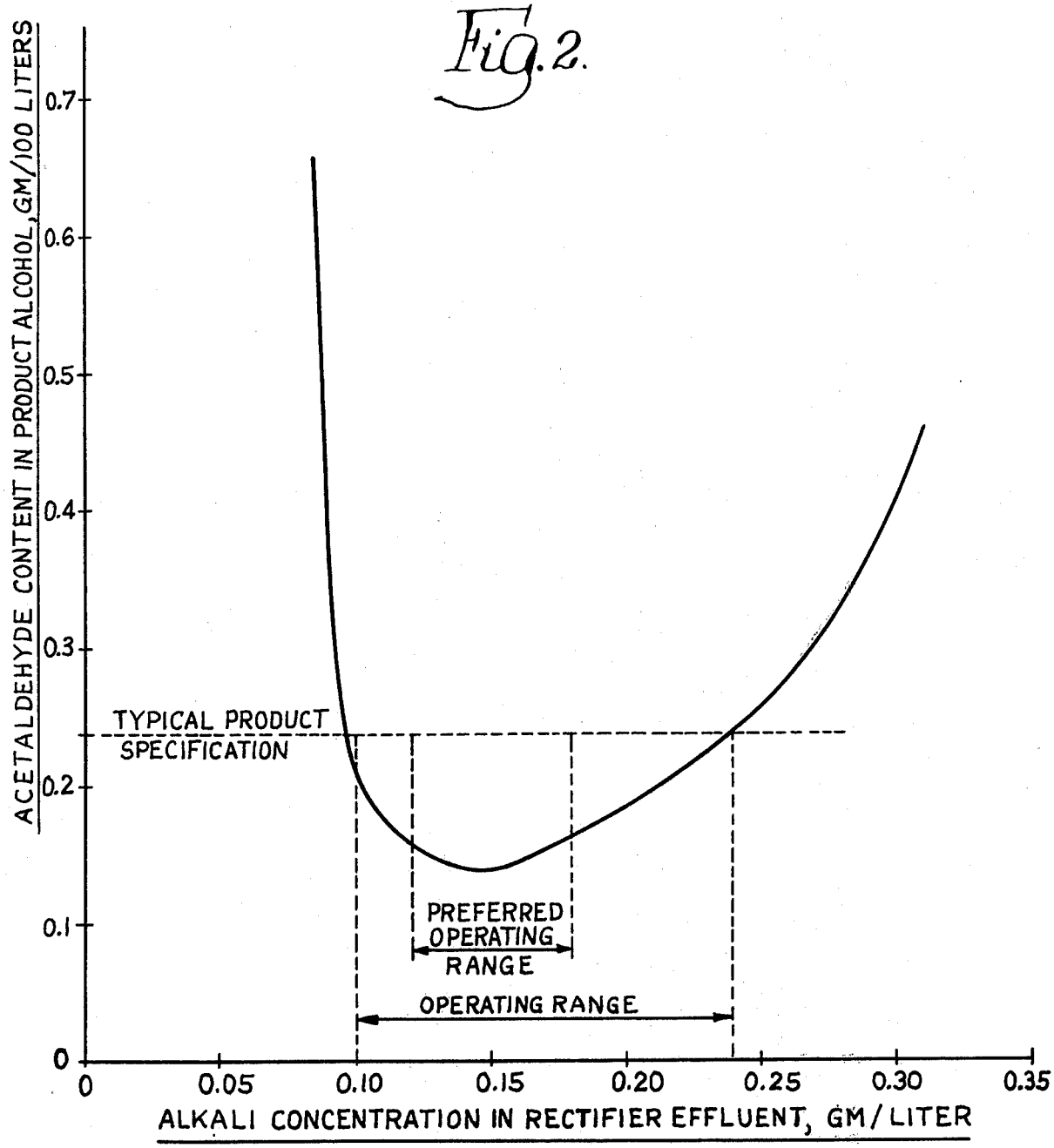

ALCOHOL DISTILLATION PROCESS

This invention relates to a novel and improved process for recovering water soluble aliphatic alcohols in highly concentrated and purified form from crude alcohol-containing mixtures. More specifically, the invention relates to an improved alkali treatment step in a multiple stage distillation process for the recovery of saturated aliphatic alcohols having not more than three carbon atoms, namely, methanol, ethanol, normal propanol, and isopropanol.

U.S. Pat. No. 3,445,345 describes a multiple stage process for purifying a crude alcohol mixture containing a saturated aliphatic alcohol having from one to three carbon atoms and associated lower boiling and higher boiling impurities by utilizing three distillation towers: (1) an extractive distillation tower, (2) a rectifying tower, and (3) an impurities concentrating tower. The crude alcohol mixture is fed to the first or extractive distillation tower which is operated at a high degree of dilution with water as the extraction medium so that substantially all of the impurities are removed in an overhead alcohol-containing stream, and a dilute aqueous stream containing from about 5 wt.% to about 10 wt.% alcohol and minor or trace amounts of impurities is withdrawn from the bottom of the tower. The bottoms stream from the first tower is fed to the second or rectifying tower which is operated to strip the desired alcohol product from the water. A purge stream containing low boiling impurities is removed overhead from the rectifying tower, and one or more purge streams containing higher boiling impurities are removed from an intermediate portion of the rectifying tower at a rate such as to permit removal of the desired alcohol product in highly concentrated and purified form from an upper portion of the rectifying tower. The stripped aqueous effluent is withdrawn from the bottom of the rectifying tower and is recycled in part to the extractive distillation tower. The overhead from the extractive distillation tower and the several purge streams from the rectifying tower are fed to the third or impurities concentrating tower which is operated so as to remove from an upper portion of the tower an alcohol stream which is recycled and combined with the crude feed to the extractive distillation tower. Low boiling impurities are recovered as an overhead product and high boiling impurities are recovered from a lower portion of the impurities concentrating tower. Stripped water is also withdrawn from the bottom of the impurities concentrating tower for discard or recycle to the extractive distillation tower.

In a multiple stage alcohol distillation system such as just described it has been found that the alcohol product occasionally contains trace impurities present in concentrations of a few parts per million or even parts per billion which cannot readily be separated by means of distillation, which cannot be identified or even detected by chemical or chromatographic analysis, but which nevertheless impart an uncharacteristic odor to what would otherwise be a high grade product. In such instances, it is known to add an aqueous solution of sodium or potassium hydroxide either to the feed to the distillation system or preferably to a suitable point in the rectifying tower. Generally, more alkali must be utilized than is consumed chemically and this is believed to be due to the need for a certain alkali concentration to cause neutralization, condensation and/or polymerization reactions of the trace impurities. For example, in the German published patent specification (Offenlegungsschrift) No. 2,106,073 it has been suggested that an aqueous alkali hydroxide solution can be introduced into the rectifying tower in amounts ranging up to 1 – 10 kg per ton of crude alcohol feed. The aqueous effluent from the bottom of the rectifying tower has a relatively high alkali content and must either be discarded or neutralized with acid prior to recycling to the extractive distillation tower. It is apparent that either procedure is wasteful of alkali and of neutralizing acid. Even if the bottoms stream is to be discarded, neutralization or other treatment will be necessary to avoid pollution when the stream is discharged to the sewer. Furthermore, in either case the large amounts of salts produced upon neutralization create additional disposal and pollution problems.

Accordingly, the general object of the present invention is to provide a novel and improved method for obtaining a high purity alcohol product in the multiple stage distillation of a crude alcohol-containing mixture.

A further object of the invention is to provide a novel and improved method of utilizing aqueous alkli reagents, such as alkali metal hydroxides, to obtain a high purity alcohol product by multiple stage distillation of a crude alcohol-containing mixture.

Another object of the invention is to provide an improved method of utilizing caustic or the like in the multiple stage distillation of a crude ethanol-containing or other alcohol-containing mixture so as to obtain a high purity alcohol product with minimal caustic consumption and minimal pollution.

Other objects and advantages of the invention will become apparent from the subsequent detailed description taken in conjunction with the accompanying drawings, wherein:

FIG. 1 is a schematic flow diagram illustrating one specific embodiment of the invention utilized for the recovery of ethanol; and FIG. 2 is a plot of operating data showing the advantage of using optimum amounts of alkali metal hydroxide in accordance with the present invention.

Although the invention is hereinafter described with specific reference to an ethanol recovery system, it is to be understood that the principles of the invention are also applicable to the recovery of methanol, normal propanol, and isopropanol.

Referring now to FIG. 1 of the drawings, the first or extractive distillation tower is designated at 10. A crude ethanol-containing feed stock, such as the crude alcohol obtained by fermentation or synthesis, is fed through a line 11 to the middle portion of the tower 10. Extraction water is fed to the top of the tower 10 through a line 12, the extraction water comprising primarily a recycle stream obtained in the manner hereinafter described. Heat is supplied at the base of the tower 10 through a heat exchanger or reboiler 16 to part of the bottoms stream circulating through lines 14 and 15 back to the base of the tower 10. Steam is supplied to the heat exchanger 16 through a line 17 in indirect heat exchange relation with the recycled bottoms stream, but it will be understood that the heat requirements of the tower 10 may also be supplied by direct introduction of steam at the base of the tower 10.

The amount of extraction water introduced through the line 12 to the top of the tower 10 and the heat input at the base of the tower 10 must be sufficient so that substantially all of the impurities, both lower boiling and higher boiling, are removed overhead from the tower 10 through a line 70. As is well understood in the art, the presence of the water in the system alters the normal volatilities of the various components so that the impurities having boiling points above that of ethanol are distilled overhead together with the lower boiling impurities. In order to achieve the desired overhead removal of the bulk of the impurities in the feed stream, the relative quantities of feed and extraction water and the heat input at the base of the tower 10 are regulated so that the bottoms stream withdrawn through the line 14 comprises a dilute aqueous alcohol stream having only minor or trace amounts of impurities and an alcohol content within the range of from about 5 wt.% to about 10 wt.% which is compatible with recovery of the final ethanol product at the required specification level in a subsequent stage of the process.

The unrecirculated portion of the dilute alcohol stream withdrawn from the base of the tower 10 is supplied from the line 14 by means of a pump 13 and a line 21 to a lower tray or portion of a rectifying or alcohol concentration tower 22. Indirect heating means, as hereinafter described, is provided at the base of the tower 22 to accomplish the desired stripping effect, but it is also within the scope of the invention to introduce steam directly into the base of the tower 22. The stripped ethanol is then concentrated in the tower 22 to the desired high concentration level (approaching the ethanol-water azeotrope composition), and a concentrated ethanol product of high purity is withdrawn and recovered through a line 24 near the top of the tower 22 as the final ethanol product of the process. As described in more detail below, a predetermined quantity of an aqueous alkali solution, for example, aqueous sodium hydroxide or potassium hydroxide and preferably sodium hydroxide, is introduced into the tower 22 through a line 23 above the point of introduction of the dilute alcohol stream through line 21 and below the point of withdrawal of the alcohol product through line 24. Although sodium and potassium hydroxides are the most feasible alkali reagents, other alkali metal compounds such as carbonates can also be used.

A "pasteurizing" or volatile fraction concentrating section in the tower 22 above the point of withdrawal of the ethanol product through the line 24 permits the accumulation and removal at low concentration levels of the lower boiling more volatile impurities or "heads" from the top of the tower 22 through a line 26. The vapors removed through the line 26 are condensed in a first condenser 27 which is supplied with cooling water through a line 28. The condensate from the condenser 27 is returned as reflux through a line 29 to the top of the tower 22. Uncondensed volatile impurities are removed through a line 31 from the condenser 27 and are supplied to a vent condenser 32 which is cooled through a line 30 either with cooling water or a refrigerant, depending upon the desirability of recovering the more volatile impurities such as diethyl ether and acetaldehyde (or other impurities such as dimethyl ether, formaldehyde, acetone, and the like, in the case of other alcohol recovery systems). The condensate from the vent condenser 32 may be returned in part as reflux to the tower 22 through a line 33 communicating with the line 29, but the remainder is removed as a purge stream through a line 34 for further processing as described below. In some cases the vent condenser 32 may be omitted, in which case a portion of the condensate stream in line 29 is withdrawn as the purge stream. By removing the overhead purge stream continuously and preferably at a steady rate, the volatile or lower boiling impurities are not permitted to accumulate to any significant extent at the point in the tower 22 where the ethanol product stream 24 is withdrawn, and the desired ethanol product is recovered through the line 24 at a very low concentration level of volatile impurities amounting to a few parts per million.

Stripped alkali-containing aqueous effluent is withdrawn from the bottom of the tower 22 through a line 19 and is recycled by a pump 20 through the line 12 to the top of the tower 10. A portion of the aqueous alkali effluent is discarded to waste through a line 25, the discarded portion being equivalent to the net water input to the system, i.e., the difference between the water in the feed and the water in the recovered product.

In addition to the overhead purge stream withdrawn through the line 34 from the rectifying tower 22, one or more intermediate purge streams containing higher boiling impurities are also removed from an intermediate portion of the tower 22 between the feed line 21 and the aqueous alkali addition line 23. The appropriate trays or points of withdrawal of the purge streams of higher boiling impurities may be selected in a well-known manner by tray composition calculations to determine the points of accumulation in the tower 22 of the higher boiling impurities, including azeotropes of these higher boiling impurities with water. Typical of such higher boiling impurities are the higher alcohols, such as butyl and amyl alcohols, as well as various aldehydes, ketones, esters, and hydrocarbons. Since the different higher boiling impurities may concentrate at several intermediate levels in the tower 22, the withdrawal of multiple purge streams is preferred to permit removal of these impurities continuously, and preferably at steady rates, thereby avoiding accumulation of the same.

In FIG. 1, removal of purge streams of higher boiling impurities from two different levels in the tower 22 is indicated by the line 36 and by the line 37 which merges with the line 36. By thus preventing accumulation of the higher boiling impurities in the tower 22, the mounts of these impurities forced up the tower 22 into the region of the ethanol product withdrawal line 24 is kept to a minimum, and the product alcohol removed through the line 24 has a very low content of higher boiling impurities (conventionally identified as "fusel oils"), for example, less than 30 parts per million and in many cases as low as 10 parts per million. Preferably, the amount of each purge stream withdrawn through the lines 34 and 36 should be from about 0.1 wt.% to about 5 wt.% of the ethanol product stream recovered from line 24.

As described in the aforementioned U.S. Pat. No. 3,445,345, the extractive distillation tower 10 and the impurities concentrating tower 42 (hereinafter described) are preferably operated at an elevated pressure of from about 25 to about 100 lbs. per sq. inch gauge and the rectifying tower 22 is operated at substantially atmospheric pressure. As a result of this difference in operating pressure, the overhead vapors from the extractive distillation and impurities concentrating towers may be condensed in reboilers at the base of the rectifying tower which normally requires the greatest heat input. Thus, the overhead impurities stream comprising both lower boiling and higher boiling impurities removed through the line 70 from the top of the extractive distillation tower 10 is passed through a reboiler or heat exchanger 71 adjacent the base of the rectifying tower 22 in indirect heat exchange relation with a portion of the bottoms stream withdrawn from the base of the tower 22 through the line 19, this portion being recirculated from the line 19 through a line 72 and the reboiler 71 and thence returned to the lower portion of the tower 22. The heat content of the overhead impurities stream at elevated pressure in line 70 causes heating of the bottom stream recirculated through the line 72, and the resultant condensed impurities stream is transferred from the reboiler 71 by a pump 75 through a line 73 to the lower portion of an impurities concentrating tower 42. Likewise, the multiple purge streams of higher boiling impurities are fed from the tower 22 through the line 36 to the lower portion of the tower 42. In addition, the overhead purge stream comprising lower boiling impurities removed from the tower 22 are introduced through the line 34 into the upper portion of the tower 42. Stripping steam is supplied directly to the base of the tower 42 through a line 43, although it will be understood that indirect heating methods may also be utilized at the base of the tower 42. The operation of the tower 42 is controlled so as to strip ethanol and the impurities from the water content of the various feeds to the tower so that water which is essentially alcohol-free may be withdrawn from the base of the tower 42 through a line 44 for discard. If desired, all or a portion of this withdrawn water may be returned, as indicated by the broken line 45, to the line 12 and thus recycled to the tower 10.

In the tower 42 the more volatile or lower boiling impurities are concentrated as heads near the top of the tower and are removed overhead through a line 74 and passed through another reboiler 76 at the base of the tower 22 in indirect heat exchange relation with another portion of the bottoms withdrawal from the tower 22, the latter being recycled from the line 19 through a line 77 and the reboiler 76 and thence back to the base of the tower 22. Thus, the heat content of the overhead elevated pressure streams from the towers 10 and 42 is utilized as a source of thermal energy for the rectifying tower 22. The condensed overhead stream is transferred from the reboiler 76 by a pump 80 through a line 78 and is thus returned in part as reflux to the top of the tower 42, the remaining portion of this stream being recovered through a line 79 as heads by-product.

Although the use of elevated pressure in the towers 10 and 42 and atmospheric pressure in the tower 22 is usually the preferred mode of operation, this is not essential, and other modes of operation may also be used (e.g., all towers at atmospheric pressure) as more fully explained in U.S. Pat. No. 3,445,345 which is incorporated herein by reference.

The ethanol content of the several impurity feed streams to the tower 42 concentrates in the upper portion of the tower 42 and is withdrawn through a line 57. This stream is recycled by a pump 50 and a line 55 to the feed line 11 and is thus combined with the crude alcohol feed and returned to the extractive distillation tower 10 for recovery of its alcohol content and re-separation of impurities therefrom. Preferably, the alcohol stream recycled through the lines 57 and 55 should contain from about 60 wt.% to about 90 wt.% ethanol and should constitute at least about 80 wt.% of the ethanol content of the total ethanol-containing streams fed to the tower 42.

In the tower 42 the higher boiling impurities concentrate at an intermediate portion of the tower between the feed point of the main impurities stream introduced through line 73 and the point of withdrawal of the recycle ethanol stream through the line 57. These impurities are withdrawn preferably from a plurality of levels such as through the line 58 and the line 59 which merges with the line 58. The concentration of higher boiling impurities in the combined stream withdrawn through the line 58 is sufficiently high so that the combined purge stream may be passed to a washer (not shown) and there contacted with an excess of water or aqueous salt solution. The higher boiling impurities comprising alcohols, esters, aldehydes, ketones, and hydrocarbons which are insoluble in the wash water or salt solution separate as an oil-like layer which can be decanted for disposal or for further treatment for by-product recovery. The water layer from the decanting step is returned to the extractive distillation tower 10 for recovery of its alcohol content and for re-separation of any dissolved impurities.

Although, as previously mentioned, the addition of aqueous alkali solution to the rectifying tower has been suggested heretofore, we have found that in a system such as described herein where the effluent water from the base of the rectifying tower is recycled to the extractive distillation tower, excessive amounts of alkali can have an adverse effect in the extraction tower, in that it can cause therein condensation and polymerization reactions of otherwise volatile substances, such as acetaldehyde, and prevent their complete removal in the extractive distillation tower. For example, in the case of acetaldehyde, a high alkali content in the extractive water can cause formation of crotonaldehyde and paraldehyde, which are very difficult to separate from the aqueous alcohol bottoms effluent streams of the extractive distillation tower When such condensation/polymerization products are carried with the aqueous alcohol stream from the base of the extractive distillation tower as feed to the rectifying tower, these products pass in part downward with the aqueous stream and are recycled to the extractive tower, while part volatilizes and, passing up through the tower, eventually escapes the alkaline zone, whereupon these products decompose, reverting to free acetaldehyde. This results in an excessive acetaldehyde content in the product alcohol, so that it cannot meet commercial specifications.

As a result of our investigation of this heretofore unidentified phenomenon we have discovered that optimum purity of the alcohol product is obtained only when the alkali treatment is conducted so that the alkali concentration in the aqueous effluent from the bottom of the rectifying tower is controlled within a narrow critical range. For example, in the case of a distillation system for the recovery of ethanol, as in FIG. 1, we have found the quality of the recovered ethanol product in terms of the key impurity, acetaldehyde, is improved rapidly with relatively low concentrations of sodium hydroxide as measured in the bottoms stream from the rectifying tower, until a minimum acetaldehyde content of the product alcohol is achieved. Addition of alkali beyond this point then results, by the mechanism indicated above, in a rapid decrease in quality as indicated by a higher acetaldehyde content in the product alcohol.

A typical commercial specification for very high grade ethanol for industrial, food or pharmaceutical use calls for a maximum of 0.24 gram of acetaldehyde per 100 liters of ethanol. It is our discovery that this stringent specification can be met only by maintaining the sodium hydroxide concentration in the stripped aqueous effluent removed through line 19 from the base of the rectifying tower 22 in the range of 0.10 to 0.24 gram per liter. Optimum quality and control at a safer level below the maximum specification is obtained by maintaining the sodium hydroxide concentration in the preferred range of 0.12 to 0.18 gram per liter. Preferably the sodium hydroxide (or other alkali) is added through line 23 as an aqueous solution having a concentration of from about 5 wt.% to about 50 wt.%. Also, the alkali treating agent should be added at a relatively high point in the rectifying tower.

Actual operating data were obtained from a commercial ethanol distillation unit conforming to FIG. 1 and using a crude feed stream derived from ethylene synthesis. In each case an aqueous solution of sodium hydroxide having a concentration of about 20 wt.% was fed to the 60% tray of the rectifying tower 22 which had 75 trays. The alkali feed rate was varied to obtain different alkali concentrations in the aqueous effluent removed from the bottom of the rectifying tower through line 19, and in each case the acetaldehyde concentration was determined in the 193 proof ethanol product removed through line 24 at the 65th–69th tray. The feed to the rectifying tower was introduced and the purge streams of high boiling impurities were removed at trays well below the point of alkali addition. The data from these tests are presented in the following Table I:

TABLE I

| Example | Feed Rate to Tower 10 (lb./hr.) | Ethanol Content of Feed (wt. %) | Acetaldehyde Content of Feed (gm.per million c.c. ethanol) | Caustic Concentration In Bottom Effluent from Tower 22 (gm./l.) | Acetaldehyde Content of Ethanol Product (gm. per 100 l. ethanol) |
|---|---|---|---|---|---|
| 1 | 117,000 | 11.95 | 1700 | 0.09 | 0.63 |
| 2 | 120,000 | 11.1 | 1900 | 0.12 | 0.16 |
| 3 | 118,000 | 12 | 1600 | 0.17 | 0.16 |
| 4 | 116,000 | 12 | 1700 | 0.26 | 0.28 |
| 5 | 118,000 | 11.95 | 1760 | 0.31 | 0.46 |

The improvement and degradation in the recovered ethanol product are shown in FIG. 2 where alkali concentration, in grams per liter, of the stripped bottoms leaving the rectifying tower and recycled to the extractive distillation tower is shown on the abscissa, while the acetaldehyde content of the product alcohol, in grams per hundred liters, is shown on the ordinate. Legends have been applied to indicate the typical commercial specification of a maximum of 0.24 gram of acetaldehyde per 100 liters of ethanol for high purity industrial alcohol and also to indicate the critical operating range for alkali concentration in the bottom effluent from the rectifying tower in accordance with the present invention.

From the foregoing it will be seen that the present invention attains the desired high quality alcohol product without the consumption of large amounts of alkali and without the necessity of discarding large amounts of waste alkali or neutralizing the same with high acid consumption. By using the specified critical amounts of alkali just sufficient to achieve the desired product quality, the recycle of alkali to the extractive distillation tower is feasible without neutralization, and it is possible to discard to the sewer only the net input of water in the feed and not the total amount of feed water plus extractive distillation water as would be the case where the aqueous alkali effluent from the bottom of the rectifying tower is discarded in to to. Moreover, the invention eliminates the necessity for neutralization with acid before recycling the aqueous bottoms to the extractive distillation tower. Thus, the invention makes it possible to realize substantial economic advantages while attaining a high quality alcohol product with reduced alkali consumption and minimal pollution problems.

We claim:

1. In a continuous process for the distillation and purification of a crude alcohol-containing mixture, wherein a feed stream containing a saturated aliphatic alcohol having not more than three carbon atoms and associated impurities is introduced into an extractive distillation tower, water is introduced into the upper portion of said extractive distillation tower, an overhead stream containing substantially all of said impurities is removed from said extractive distillation tower, a dilute aqueous stream containing a low concentration of said alcohol is withdrawn from the bottom of said extractive distillation tower and is introduced into a rectifying tower, a desired alcohol product is withdrawn and recovered from the upper portion of said rectifying tower, and a stripped aqueous effluent stream is withdrawn from the bottom of said rectifying tower and a part thereof is recycled to the upper portion of said extractive distillation tower, and wherein said alcohol product may contain trace impurities which cannot readily be separated by distillation;

the improved method of removing said trace impurities without adversely affecting the operation of said extractive distillation tower which comprises:

introducing into said rectifying tower an aqueous solution of an alkali metal compound selected from the group consisting of the alkali metal hydroxides and carbonates; and regulating the feed rate of said aqueous solution to said rectifying tower so that the concentration of said alkali metal compound in said stripped aqueous effluent stream withdrawn from the bottom of said rectifying tower is from about 0.10 to about 0.24 gram per liter;

the recycled part of said stripped aqueous effluent stream being recycled to said extractive distillation tower without neutralization.

2. The process of claim 1 further characterized in that said alkali metal compound concentration is from about 0.12 to about 0.18 gram per liter.

3. The process of claim 1 further characterized in that said alkali metal compound is sodium hydroxide.

4. The process of claim 1 further characterized in that said alcohol is ethanol.

5. In a continuous process for the purification of crude alcohol-containing mixtures comprising introducing into the middle portion of a first distillation tower comprising an extractive distillation zone a feed stream containing a saturated aliphatic alcohol having not more than three carbon atoms and associated lower boiling and higher boiling impurities; introducing water into the upper portion of said first distillation tower; removing an overhead stream from said first distillation tower containing substantially all of said impurities; withdrawing from the bottom of said first distillation tower a dilute aqueous stream containing said alcohol at a concentration of from about 5 wt.% to about 10 wt.% and also containing minor amounts of said lower boiling and said higher boiling impurities; introducing said dilute aqueous stream withdrawn from the bottom of said first distillation tower into a second distillation tower comprising a rectifying or alcohol concentrating zone; withdrawing and recovering from the upper portion of said second distillation tower an alcohol product stream comprising said alcohol in highly concentrated and purified form; withdrawing a stripped aqueous effluent stream from the bottom of said second distillation tower and recycling the same in part to the upper portion of said first distillation tower; withdrawing from said second distillation tower an overhead purge stream containing said lower boiling impurities; withdrawing from an intermediate portion of said second distillation tower at least one purge stream containing said higher boiling impurities; introducing into a third distillation tower comprising an impurities concentrating zone said purge streams from said second distillation tower and said overhead stream from said first distillation tower; withdrawing from said third distillation tower said lower boiling and said higher boiling impurities; and withdrawing from said third distillation tower an alcohol-containing stream and recycling the same to said first distillation tower in combination with said feed stream; and wherein said alcohol product stream may contain trace impurities which cannot readily be separated by distillation;

the improved method of removing said trace impurities without adversely affecting the operation of said first distillation tower which comprises:

introducing into said second distillation tower, below the point of withdrawal of said alcohol product stream but above the point of introduction of said aqueous stream from the bottom of said first distillation tower, an aqueous solution of an alkali metal compound selected from the group consisting of the alkali metal hydroxides and carbonates; and regulating the feed rate of said aqueous solution to said second distillation tower so that the concentration of said alkali metal compound in said stripped aqueous effluent stream withdrawn from the bottom of said second distillation tower is from about 0.10 to about 0.24 gram per liter;

the recycled part of said stripped aqueous effluent stream being recycled to said first distillation tower without neutralization.

6. The process of claim 5 further characterized in that said alcohol is ethanol.

7. The process of claim 5 further characterized in that said alkali metal compound is sodium hydroxide.

8. The process of claim 5 further characterized in that the concentration of said alkali metal compound is from about 0.12 to about 0.18 gram per liter.

9. The process of claim 5 further characterized in that the acetaldehyde content of the ethanol product stream is not greater than about 0.24 gram per 100 liters of ethanol.

10. The process of claim 1 further characterized in that said aqueous solution is the sole treating agent introduced into said rectifying tower for removing said trace impurities, and the essential active ingredient of said aqueous solution consists of said alkali metal compound.

11. The process of claim 1 further characterized in that sid alkali metal compound is sodium hydroxide and said alcohol is ethanol.

12. The process of claim 11 further characterized in that the concentration of said sodium hydroxide is from about 0.12 to about 0.18 gram per liter.

13. The process of claim 5 further characterized in that said aqueous solution is the sole treating agent introduced into said second distillation tower for removing said trace impurities, and the essential active ingredient of said aqueous solution solution consists of said alkali metal compound.

14. The process of claim 5 further characterized in that said alcohol is ethanol and said alkali metal compound is sodium hydroxide.

15. The process of claim 14 further characterized in that the concentration of said sodium hydroxide is from about 0.12 to about 0.18 gram per liter.

16. The process of claim 14 further characterized in that the acetaldehyde content of the ethanol product stream is not greater than about 0.24 gram per 100 liters of ethanol.

* * * * *

UNITED STATES PATENT OFFICE
CERTIFICATE OF CORRECTION

PATENT NO. : 3,990,952
DATED : November 9, 1976
INVENTOR(S) : Raphael Katzen and Vincent B. Diebold It is certified that error appears in the above—identified patent and that said Letters Patent are hereby corrected as shown below:

Column 10, line 20, "claim 5" should read --claim 11--;

line 32, "sid" should read --said--; and line 41, "solution solution" should read --solution--.

Signed and Sealed this

Fifteenth Day of March 1977

[SEAL]

Attest:

RUTH C. MASON
Attesting Officer

C. MARSHALL DANN
Commissioner of Patents and Trademarks